United States Patent [19]

Olexa et al.

[11] 4,455,290

[45] Jun. 19, 1984

[54] INHIBITION OF FIBRIN POLYMERIZATION BY A PEPTIDE ISOLATED FROM FIBRIN FRAGMENT $D_1$

[75] Inventors: Stephanie A. Olexa, Hellertown; Andrei Z. Budzynski, Glenside, both of Pa.

[73] Assignee: Research Corporation, New York, N.Y.

[21] Appl. No.: 250,173

[22] Filed: Apr. 2, 1981

[51] Int. Cl.$^3$ .................. A61K 49/00; A61K 43/00
[52] U.S. Cl. ........................................ 424/1.1; 424/4; 424/5; 424/177; 260/112.5 R; 252/645
[58] Field of Search .................... 424/1, 4, 5, 177; 260/112.5

[56] References Cited

U.S. PATENT DOCUMENTS

| | | | |
|---|---|---|---|
| 3,933,996 | 1/1976 | Charlton et al. | 424/1 |
| 4,057,617 | 11/1977 | Abramovici et al. | 424/1 |
| 4,245,051 | 1/1981 | Reich et al. | 424/101 |

OTHER PUBLICATIONS

Budzynski et al., Biochim. Biophys. Acta, 584(1979) 284–287.
Olexa et al., Biochem., 18(1979) 991–995.
Olexa et al., Biochem. 20(1981) 6139–6145.
Olexa et al., Biochim. Biophys. Acta, 576(1979) 39–50.
Hoots et al., N.E. J. Med., 304(4-9-1981) 857–861.
Kisiel et al., Biochem. 15(1976) 4893–4900.
Niemann et al., Biochem., 19 (1980) 1576–1583.
Scully et al., Biochem. Biophys. Res. Comm., 68 (1976) 1206–1211.
Mosher, J. Biological. Chem., 251(1976) 1639–1645.

Primary Examiner—Christine M. Nucker
Attorney, Agent, or Firm—Scully, Scott, Murphy & Presser

[57] ABSTRACT

A purified peptide isolated from fibrinogen Fragment $D_1$ and having the amino acid sequence Thr-Arg-Trp-Tyr-Ser-Met-Lys-Lys-Thr-Thr-Met-Lys-Ile-Ile-Pro-Phe-Asn-Arg-Leu-Thr-Ile-Gly-Glu-Gly-Gln-Gln-His-His-Leu-Gly-Gly-Ala-Lys-Gln-Ala-Gly-Asp-Val. The peptide is isloated by degrading Fragment $D_1$ of fibrinogen with plasmin followed by separation of the resulting peptides on the basis of molecular weight and affinity for bound fibrin monomer. The purified peptide is useful as an anticoagulant and, when suitably labeled with a gamma-emitting radioisotope, as a thrombus imaging agent.

24 Claims, 7 Drawing Figures

INHIBITION OF FIBRIN POLYMERIZATION BY A PEPTIDE ISOLATED FROM FIBRIN FRAGMENT D$_1$

BACKGROUND OF THE INVENTION

1. Field of the Invention

This invention relates to the inhibition of blood coagulation and more particularly to the inhibition of fibrin polymerization by a novel peptide isolated from fibrin Fragment D$_1$ and to the peptide itself, its isolation, and its additional uses.

2. Description of the Prior Art

Anticoagulants and antithrombic agents are among the most important drugs presently available for the treatment and prevention of intravascular clotting disorders, currently a major cause of death and disease in Western society. The process of thrombus formation is only incompletely understood, but appears to consist of two major stages. Initially, platelets present in the blood aggregate at the site of a blood vessel injury followed by formation of a cross-linked fibrin polymer which binds the forming clot together. Working to counteract this tendency and to dissolve clots are fibrinolytic enzymes that tend to break down the fibrin polymer and dissolve the clot. Therefore, there are at least three steps at which drugs may work: (1) prevention of platelet aggregation, (2) prevention of the formation of the fibrin polymer, and (3) enhancement of fibrinolytic activity. The present invention is related to the second type of action.

One way of providing such an anticoagulant, not fully developed prior to the present invention, is through interference with the polymerization process by use of a competitive inhibitor derived from the natural binding site involved in the polymerization reaction. This could not be realized until the binding site on Fragment D could be located. Although the binding site of polymerization was not specifically located until the present invention, other aspects of the polymerization process had been investigated. Fibrin polymerization in humans begins when fibrinogen is converted to fibrin through a limited proteolytic cleavage by the enzyme thrombin. Thrombin cleaves the bonds A$\alpha$16 Arg-17 Gly and B$\beta$14 Arg-15 Gly, releasing two molecules of fibrinopeptide A and two molecules of fibrinopeptide B from the dimeric fibrinogen molecule and leaving behind a fibrin monomer capable of polymerization. The removal of fibrinopeptide A by thrombin proceeds at a much faster rate than that of fibrinopeptide B; however, the removal of fibrinopeptide A alone is sufficient for polymerization to occur.

It has been postulated that polymerization of fibrin monomer molecules takes place through two proceses, initially by an end-to-end association of molecules forming a fibrin strand and secondarily, by a lateral association of the strands. Light scattering has been used to differentiate between the two steps in polymerization. Recently the same technique was used to demonstrate that the removal of fibrinopeptide A led to the polymerization of fibrin monomers to form protofibrils and that the effect of the removal of fibrinopeptide B is an enhancement of the rate of lateral association of protofibrils.

Recent investigations have focused on defining areas of the fibrin monomer molecule that participtate in polymerization by identifying binding properties of degradation products of fibrinogen or fibrin. It has been shown that a certain abnormal fibrinogen has a functional binding site in the Fragment D domain but a defective site in the NH$_2$-terminal region. This fibrinogen variant contains a single amino acid substitution, A$\alpha$19 Arg→Ser, suggesting that the NH$_2$-terminal binding site is at or near residue 19 on the A$\alpha$ chain. Recently, evidence was provided that the tripeptide Gly-Pro-Arg, which is contiguous with fibrinopeptide A, binds to fibrinogen and inhibits fibrin monomer polymerization. This suggests that an NH$_2$-terminal binding site is located on the A$\alpha$ chain of fibrinogen immediately following fibrinopeptide A.

It has been postulated that the Fragment D binding site is located on either the NH$_2$-terminal or COOH-terminal region of the $\gamma$ chain remnant of the Fragment D. However, the Fragment D binding site was not known prior to the present invention.

Although the binding-site was not known, several drugs that interfere with the formation of cross-linked fibrin were known, for example, heparin, the coumarins, and the indanedione drugs. The point of action and the mechanism of these drugs is not completely understood, and some undesirable side effects are known. For example, heparin has been known to occasionally cause severe thrombocytopenia (decrease in the number of platelets). The orally administered coumarins can cause nonspecific dermatitis and even skin necrosis. The indanediones (e.g. phenindione) have antithyroid activity and can cause liver and kidney damage. Accordingly, other anticoagulants, having a known and specific course of action and therefore being more easily controllable, are highly desirable.

SUMMARY OF THE INVENTION

Accordingly, it is an object of this invention to provide a method of preventing the formation of thrombi that relies on specific, competitive inhibition of the polymerization of fibrin monomers.

It is a further object of this invention to provide a fibrin polymerization inhibitor isolated from substances normally found in the blood in order to minimize allergic reactions.

It is still another object of this invention to provide a substance isolated from the blood that has no function other than fibrin polymerization inhibition in order to reduce undesirable side effects.

It is yet another object of this invention to provide a competitive inhibitor of fibrin polymerization derived from the Fragment D binding site of the fibrin monomer.

It is a still further object of this invention to provide a method of isolating the fibrin polymerization inhibitor in order that it be made readily available.

These and other objects of the invention as will hereinafter become more readily apparent have been attained by providing a purified peptide isolated from the D$_1$ fragment of fibrinogen and having the amino acid sequence Thr-Arg-Trp-Tyr-Ser-Met-Lys-Lys-Thr-Thr-Met-Lys-Ile-Ile-Pro-Phe-Asn-Arg-Leu-Thr-Ile-Gly-Glu-Gly-Gln-Gln-His-His-Leu-Gly-Gly-Ala-Lys-Gln-Ala-Gly-Asp-Val.

The D$_1$ Peptide may be isolated by degrading the Fragment D$_1$ of fibrinogen with plasmin, selectively separating peptides having a molecular weight of less than 10,000 daltons and selectively separating said D$_1$ Peptide from said peptides by affinity chromotography.

The $D_1$ Peptide has been demonstrated to be a competitive inhibitor of fibrin monomer polymerization and can be used as an anitcoagulant by administering to a patient an effective amount of $D_1$ Peptide sufficient to lengthen clotting time as measured by the thrombin time test, or by adding to a container of blood an amount of $D_1$ Peptide sufficient to delay clotting.

In addition, the $D_1$ Peptide has been shown to be of use in the detection of a thrombus by administering to a human or animal an amount of $D_1$ Peptide labeled with a gamma-emitting radioisotope sufficient to allow external detection of the location of the thrombus.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 3 shows inhibition of fibrin monomer polymerization by $D_1$ Peptide. The polymerization of thrombin fibrin monomer was measured continuously for 15 min., recording the change of absorbance at 350 nm. The $D_1$ Peptide was mixed with the fibrin monomer in various molar ratios and polymerization monitored. Curves for batroxobin fibrin monomer were similar;

DESCRIPTION OF THE PREFERRED EMBODIMENTS

A peptide identified hereafter as the $D_1$ Peptide has been isolated from the γ chain remnant of fibrinogen Fragment $D_1$ and has the ability to bind to the NH$_2$-terminal region of fibrinogen as well as to inhibit fibrin monomer polymerization.

$D_1$ Peptide, which is a small part of the Fragment $D_1$ of fibrinogen, can be isolated from fibrinogen after suitable steps of enzymatic cleavage and purification. Fibrinogen from humans or warm-blooded animals, such as rabbits, pigs, horses, etc., may be used, but a preferred source is the same type of organism in which the $D_1$ Peptide is to be used, e.g. human fibrinogen as a source of human $D_1$ Peptide. The fibrinogen is dissolved or suspended in an aqueous buffer and digested with plasmin or with plasminogen and streptokinase or another plasminogen-activating enzyme. The resulting digest contains primarily Fragments $D_1$ and $E_3$ from the fibrinogen. The components of the digest are separated by any means suitable for separation of proteins and peptides by molecular weight, preferably by gel filtration through a 3-9% agarose gel, and most preferably using 6% agarose gel beads, having a particle size of 40-210µ in the wet state, and with an approximate exclusion limit for proteins of $4 \times 10^6$ daltons (e.g. Sepharose® CL-6B). If a gel filtration column is used, about 0.5-20 cm$^3$ of gel beads per mg of digest is preferred with about 1-8 cm$^3$/mg being most preferred. Suitable buffers for elution may have any pH between 1 and 14; preferred are those having a pH between 4 and 10. Most preferred are buffers made from volatile components, such as ammonium carbonate buffers between 0.01 and 0.5M. Buffers made from volatile components allow freeze drying at any stage of purification, a desirable characteristic that allows purification to be carried out with greater convenience. Fragments $D_1$ and $E_3$ are not separable from each other at this point on the basis of molecular weight, but α chain remnants and any higher molecular weight fragments are removed. Since Fragment $E_3$ is resistant to further digestion, its separation is not essential at this point, although any method that separated Fragment $D_1$ from Fragment $E_3$ could be used at this point if desired.

The digest containing Fragment $D_1$, either alone or in the presence of fragment $E_3$, is next digested further with plasmin or a combination of reagents capable of producing plasmin as previously described. This digestion may be preceded by dialysis to remove calcium ions. Calcium ions interfere with further digestion by plasmin and must be removed, preferably to give a concentration of less than $10^{-5}$M, most preferably less than $10^{-6}$M. The dialysis medium preferably contains disodium ethylenediaminetetraacetate (EDTA) or any other calcium ion chelating agent, most preferably in a buffer having physiological conditions of ionic strength and pH. Digestion conditions may vary somewhat, but should give Fragments $D_2$ and $D_3$ with γ-chains having a molecular weight of about 32,000 and 26,000 daltons, respectively. Suitable digestions include digestion for from 10 to 40 hours at from 39° to 20° C. Longer digestion times do not greatly adversely affect formation of the $D_1$ Peptide. Shorter digestion times result in incomplete digestion and lower yields, but otherwise have no effect. As is well known, higher temperatures correspond to shorter digestion times and vice versa. In addition, the amount of plasmin may be varied and the digestion can be controlled by changing the time and temperature of incubation. Other enzymes, such as trypsin, chymotrypsin, or endopeptidase may produce peptides similar to $D_1$ Peptide with the same or slightly modified binding properties. Preferred is digestion with plasmin for from 4 to 24 hours at 35° to 39° C. Most preferred is digestion overnight at approximately 37° C. The components of the resulting digest are separated according to molecular size, preferably by chromatography on a polyacrylamide, agarose, or dextran gel. Most preferred are dextran gel beads having a dry diameter of 40–120μ and being capable of separating peptides and globular proteins in the range of 5,000–400,000 daltons (e.g., Sephadex G-100). If a chromatography column is used, about 5–100 cm³ of gel beads per 1 gram of original fibrinogen is preferred with 10–50 cm³/g being most preferred. Since separation of proteins by molecular weight may be achieved without retaining their conformations, control of pH in the eluent is not essential. However, preferred eluents are acetic acid solutions, most preferably at about 1–16% concentration, since acetic acid solutions modify high molecular weight proteins and cause them to aggregate, resulting in greater ease of separation. Acetic acid also solubilizes the peptides to keep them in solution and is quite volatile, making it easily removable by freeze drying, thereby concentrating the peptides. Any separation technique that separates peptides having a molecular weight of less than 10,000 from higher molecular weight peptides and proteins is suitable at this stage of the purification. The peptides having molecular weights less than 10,000 daltons eluting from the column can be used directly in the next step of the purification or can be freeze dried and stored for later use.

The relatively low molecular weight peptides available at this point in the purification process are further purified by affinity chromatography or any other method capable of separating peptides having binding affinity for fibrin monomers from other peptides. If affinity chromatography is used, insolubilized fibrin monomer is prepared by any method that will not interfere with later binding by the peptides. A preferred method uses fibrinogen insolubilized on cyanogen bromide-activated agarose gel beads and then converted to fibrin monomer by the action of the enzyme thrombin. Any thrombin is suitable; human α-thrombin is preferred.

A column or other suitable form prepared from the agarose-fibrin conjugate is equilibrated in buffer before the peptide digest is applied. The pH needs to be controlled since the conformation of the various peptides should be disturbed as little as possible. Suitable buffers have a pH from 6 to 8; preferred is a pH of about 7.6; most preferred is a 0.1M ammonium bicarbonate buffer, pH 7.6. Salt concentration also needs to be controlled during this stage of the separation. Ammonium carbonate buffers having a concentration of less than 0.5M are suitable; preferred are those between 0.05 and 0.3M, most preferred is 0.1M. Other volatile buffers of equivalent ionic strength can also be used. The low molecular weight peptides are applied to the column, preferably at a concentration of 1.0 absorbance unit at 280 nm per 1–50 cm³ of agarose-fibrin monomer. Most preferred is a concentration of 1.0 absorbance unit at 280 nm for about 5 cm³ of agarose-fibrin monomer prepared by the above-described cyanogen bromide-activation method. However, the activity of an affinity column varies somewhat with each column preparation, as is well known in the art, and some adjustment of concentration may be necessary. Unbound material is removed by washing with the equilibration buffer or an equivalent buffer. The bound material can be eluted with a high-salt solution (e.g., 2–3) (M NaCl or KSCN), a base solution, or an acid solution; preferred are acid solutions having a pH of less than 5; most preferred is 10% acetic acid. The material eluted at this point is the $D_1$ Peptide.

The structure of the $D_1$ Peptide has been determined by a combination of experimental evidence. The total amino acid composition was determined by hydrolysis of the $D_1$ Peptide and identification of the released amino acids. In addition, the sequence of amino acids at both the COOH and $NH_2$ ends of the $D_1$ Peptide was determined. Since the amino acid sequence of the various chains of fibrinogen is known, the sequence corresponding to the $D_1$ Peptide could be determined. This was found to be amino acid residues 373–410 of the γ chain (the COOH-terminal of the γ chain). The amino acid sequence of the $D_1$ Peptide is as follows: Thr-Arg-Trp-Tyr-Ser-Met-Lys-Lys-Thr-Thr-Met-Lys-Ile-Ile-Pro-Phe-Asn-Arg-Leu-Thr-Ile-Gly-Glu-Gly-Gln-Gln-His-His-Leu-Gly-Gly-Ala-Lys-Gln-Ala-Gly-Asp-Val.

Since the amino acid sequence is known, the $D_1$ Peptide can be synthesized by standard techniques of peptide synthesis.

Preliminary evidence indicates that not all of the amino acids in the $D_1$ Peptide are essential for binding to fibrin. Enzymatic cleavage of amino acids from the $NH_2$-terminal of $D_1$ Peptide indicates that the actual binding site may be in the 5–7 amino acids at the carboxy terminal of the $D_1$ Peptide. These amino acids are X-Gln-Ala-Gly-Asp-Val, where X represents Ala-Lys-, Lys-, or the absence of any amino acid. Intermediate peptides between these and the $D_1$ Peptide also retain binding affinity for the fibrin molecule. Intermediate peptides, or X-Gln-Ala-Gly-Asp-Val, are easily obtained from the $D_1$ Peptide through the action of enzymes such as trypsin, chymotrypsin, or endopeptidase, or synthesized by standard techniques of peptide synthesis.

In addition, other derivatives of these peptides having substantially the same amino acid sequences except for minor modifications, such as, for example, a specific amino acid being replaced by a different amino acid having similar properties or a hydrogen being replaced by a different organic radical or metal ion, are considered to be within the scope of the present invention. Such derivatives having a relative binding affinity of 5% or more of that of the $D_1$ peptide would be suitable for the same uses as described herein for the $D_1$ Peptide and other fibrin-binding peptides. Preferred are derivatives having a relative binding affinity of 20% or more.

The $D_1$ Peptide has been shown to inhibit fibrin monomer polymerization using standard techniques previously used to determine polymerization inhibition by Fragments X and Y and by other fibrinogen fragments. As the molar ratio of $D_1$ Peptide to fibrin monomer increased, the maximum rate of polymerization and the extent of polymerization at 15 min. after polymerization was initiated both decreased, and the lag time before polymerization began increased. The maximum rate decreased by 50% at a molar ratio of 1:1 (see Examples). The effect of the $D_1$ Peptide is to decrease the apparent concentration of polymerizable species of fibrin monomers, thereby acting as a competitive inhibitor of fibrin monomer polymerization.

Because of this effect, the $D_1$ Peptide should be useful as an anticoagulent. Intravenous injection is a preferred method of use. Suitable amounts for injection would vary according to the clinical needs of the patient, and the amount of anticoagulation desired. A 50% increase in thrombin time could be caused by creating a blood concentration of about $4.4 \times 10^{-6}M$. This could be achieved by an intravenous injection of about 1.9 mg to 2.9 mg of $D_1$/kg of body weight. Preferred is about 2.4 mg/kg. Achievement of the desired increase in blood clotting time can easily be determined by the examining physician using standard assay techniques (e.g., measurement of thrombin time) after injection of a trial dose. A suitable initial dose would be about 0.2 to 0.3 mg/kg. However, $D_1$ Peptide is not expected to cause internal bleeding in large doses as may occur with known anticoagulants and may be administered in a larger initial dose if desired. Administration may be discontinuous by intermittent injection or continuous by intravenous injection.

$D_1$ Peptide may be administered by injection via a suitable pharmaceutical carrier, either alone or in combination with another drug. Suitable pharmaceutical carriers are those which dissolve $D_1$ Peptide or hold it in suspension, and which are not toxic to the extent of permanently harming the host organism. Preferred are aqueous solutions of salts or non-ionic compounds such as sodium chloride or glucose, most preferably at an isotonic concentration. Other drugs may be present provided that they do not interfere with the ability of $D_1$ Peptide to bind to the fibrin binding site. Suitable weight percentages for mixtures are 5–95% $D_1$ Peptide and 95–5% other drug or drugs. Particularly suitable are other anticoagulents, such as heparin, phenprocoumon, warfarin sodium, nicoumalone, cyclocoumarol, ethyl biscoumacetate, phenindione, diphenadione, anisindione, or chlorophenylindanedione.

$D_1$ Peptide may be injected into the blood stream at any convenient point, although injection upstream from and near to the site of the suspected or known thrombus is preferred.

In addition to its use as an anticoagulant in humans, $D_1$ peptide may also be used in veterinary medicine. In such cases, $D_1$ peptide is preferably isolated from the same species of animal in which it is used, although cross-species use is permissible. In general, use in animals resembles use in humans, with the exception that some variation in dosage requirements between species is expected. A typical dose would be about 1 to 4 mg/kg. As with humans, the actual dose required can be determined by simple experimentation with dosages followed by measurement of prothrombin time. A suitable initial dose is from 1 to 2 mg/kg.

$D_1$ Peptide may also be used to prevent clotting in in vitro blood containers. Experiments have shown that a 1:1 ratio of $D_1$ Peptide to fibrinogen in the presence of thrombin delays the onset of fibrin polymerization for 8 minutes. The delay in onset of fibrin polymerization varies directly with the amount of $D_1$ Peptide present, as is expected for competitive inhibitors. Accordingly, $D_1$ Peptide may be used as an in vitro anticoagulent, for example, in blood sample containers or artificial kidney machines, when present in an amount sufficient to prevent fibrin polymerization from occurring. Polymerization may be mildly or strongly inhibited as may be desired by varying the concentration of $D_1$ Peptide present.

Yet a further use of $D_1$ Peptide results from its ability to bind with fibrin that has already entered into the clotting process. When labeled with a suitable radioisotope, $D_1$ Peptide enters into a forming clot and allows detection of the location of a thrombus by external detection of emitted radiation. Suitable radioisotopes are well known and include $^{125}I$, $^{131}I$, and $^{99}Tc$. Similar thrombus-imaging agents, for example, fibrinogen labeled with radioactive iodine (U.S. Pat. No. 3,933,996) or radioactive technetium (U.S. Pat. No. 4,057,617), are well known.

When $D_1$ Peptide is used as an imaging agent, it should be administered in an amount sufficient to be detected by scintillation scanning or other external radiation detection means capable of locating the localized radiation present in the thrombus, such as autoradiography. In general, about 5 to 20 $\mu Ci$ should be administered; most preferred is about 10 $\mu Ci$. The actual amount depends on the location of the thrombus as is well known in the art. Additional radioactive $D_1$ Peptide may be injected if necessary up to the amounts limited by prevalent standards of safety.

Imaging by scintillation scanning may begin within 1–15 minutes after injection. Better results are generally obtained between 1 and 5 hours after injections. $D_1$ Peptide is rapidly eliminated from the blood, an advantageous characteristic for an imaging agent. $D_1$ Peptide also has a high affinity for fibrin and should remain in a thrombus until the thrombus itself is degraded or lysed in the blood. This varies with the physiological condition of the patient, and would vary from a few hours in a patient with high fibrinolytic activity whose thrombus is in the process of dissolving, to many days in the case of a patient in whom active thrombus formation is taking place. In the latter case, the incorporated $D_1$ Peptide would be protected from degradation by new layers of forming thrombus.

In terms of amount by weight of radioactive $D_1$ Peptide that is administered, no apparent lower limit exists except for the degree to which $D_1$ Peptide is labeled with a radioactive isotope. There does not appear to be any upper limit except for those created by solubility for $D_1$ Peptide isolated from the same species into which it is injected. An upper limit is set for injections from a different species by immune reactions, as is well known in the art and determinable by simple experimentation. If the specific radioactivity of the $D_1$ Peptide is known, and the desired radioactivity is known as previously described, the amount of $D_1$ Peptide injected can be easily calculated. For example, if the specific activity is 2 $\mu Ci/mg$, a 5 mg sample would contain 100 $\mu Ci$ of radioactivity.

In addition, $D_1$ Peptide labeled with an X-ray contrast agent may similarly be used in the location of thrombi. An element that absorbs X-radiation may be attached to the $D_1$ Peptide so that the thrombus absorbs X-radiation and casts a shadow on X-ray film. The X-ray absorbing agent may be attached covalently or in any other way that results in long term association with the $D_1$ Peptide, for example by chelation. Such a preparation would be administered in a manner similar to that described above for $D_1$ Peptide labeled with gamma-emitting radioactive isotopes.

Having generally described the invention, a more complete understanding can be obtained by reference to certain specific examples, which are provided herein for purposes of illustration only and are not intended to be limiting unless otherwise specified.

EXAMPLES

Isolation of $D_1$ Peptide

Figure 1:
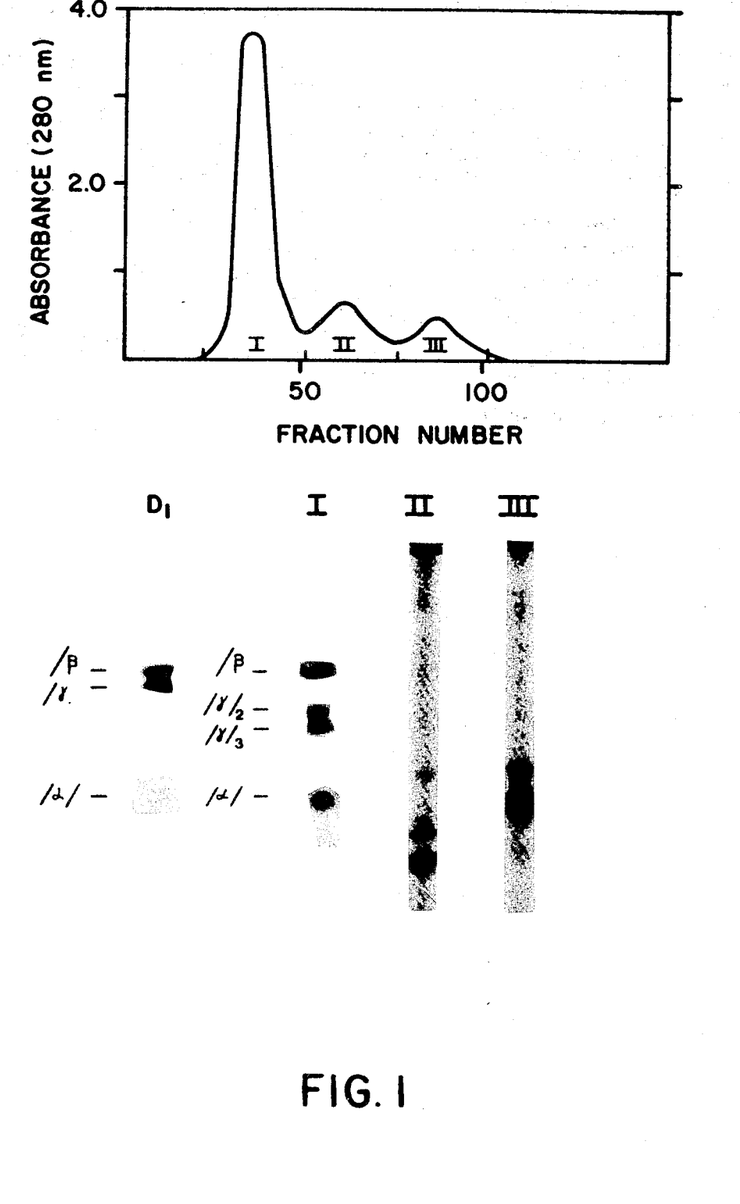
FIG. 1 shows gel filtration profile of plasmin digested Fragment $D_1$ on a Sephadex G-100 column (2×90 cm) in 10% acetic acid. Fractions (2 ml) were collected and the absorbance at 280 nm was determined. In the lower half of the figure SDS polyacrylamide gels (7%) under reducing conditions of the undigested Fragment $D_1$ and Fragments $D_2$, $D_3$ (Pool I) are shown. Pools II and III were electrophoresed on 12.5% polyacrylamide gels with SDS under reducing conditions.

One gram of human fibrinogen (Grade L), in 0.15M Tris-HCl, 10 mM calcium chloride, pH 7.4 was digested by 100 units of plasminogen and 20,000 units of streptokinase to obtain a digest containing primarily Fragments $D_1$ and $E_3$ as has been described previously in Budzynski et al, *J. Biol. Chem.* 249, 2294–2302 (1974) and Purves et al, *Thromb. Res.* 12, 473–484 (1978) which are hereby incorporated by reference. Approximately 250 mg of the digest was gel filtered on a Sepharose CL-6B column (2.5×190 cm) in 0.1M ammonium bicarbonate buffer, pH 7.6 to separate $D_1$ Fragment from $\alpha$ chain remnants and any higher molecular weight fragments. Fragments $D_1$ and $E_3$ cannot be separated by this technique; however, Fragment $E_3$ is resistant to further digestion. The Fragment $D_1$ which was isolated by gel filtration consisted of three polypeptide chains of different molecular weights: $/\alpha/$, 12,000; $/\beta/$, 43,000; and $/\gamma/$, 39,000, as seen on 7% polyacrylamide gel electrophoresis under reducing conditions (FIG. 1). The reduced chains of Fragment $E_3$ had much faster electrophoretic mobility under these conditions and were not seen. The Fragment $D_1$ preparation was dialyzed against 0.1M ammonium bicarbonate, 0.025M EDTA, pH 7.6, then digested (plasminogen 100 units/g $D_1$; streptokinase 20,000 units/g $D_1$) in the dialysis buffer at 37° C. overnight, to give Fragments $D_2$ and $D_3$ with $/\alpha/$ 12,000, $/\beta/$, 43,000, and $/\gamma/$, 32,000 and 26,000, respectively. The contaminating Fragment $E_3$ is resistant to further digestion under these conditions. The digested $D_1$ preparation was gel filtered on a 2.0×9.0 cm Sephadex G-100 column in 10% acetic acid to separate cleaved peptides from the Fragments $E_3$, $D_2$, and $D_3$ (FIG. 1). Peak I was tested on 7% polyacrylamide sodium dodecylsulfate (SDS) gels, and Peaks II and III were analyzed on 12.5% polyacrylamide (SDS) gels. Peak II contained at least four peptides while Peak III contained two peptides of approximate molecular weights 5,000 and 5,500. The peptides were freeze-dried, suspended in 0.1M ammonium bicarbonate pH 7.6 and further purified by affinity chromatography on insolubilized fibrin monomer.

The insolubilized fibrin monomer was prepared by insolubilizing fibrinogen on cyanogen bromide-activated Sepharose and converting the fibrinogen to fibrin monomer by thrombin (human $\alpha$-thrombin) as has been previously described in Heene et al, *Thromb. Res.* 2, 137–154 (1973), which is hereby incorporated by reference. The Sepharose-fibrin monomer column (1×5 cm) was equilibrated in 0.1M ammonium bicarbonate pH 7.6, and peptide corresponding to 1.0 absorbance unit at 280 nm was applied to the column. Unbound material was removed by washing with the equilibration buffer, and bound peptide was eluted with 10% acetic acid. The concentration of the purified peptide solution was determined by the method of Bradford, *Anal. Biochem.* 72, 248–254 (1976), which is hereby incorporated by reference.

Figure 2:
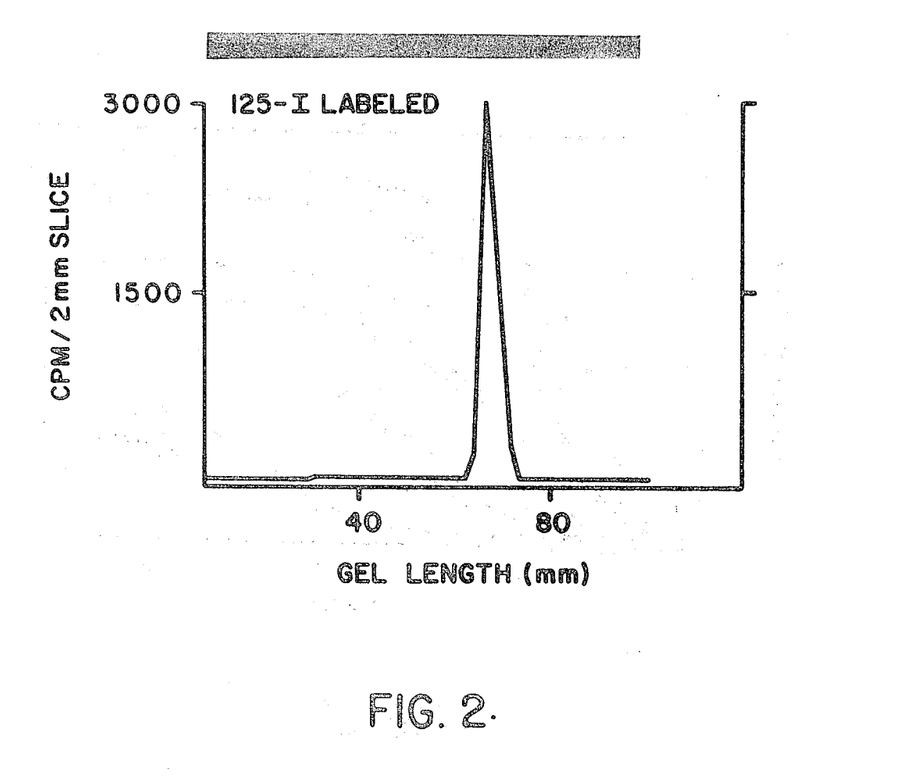
FIG. 2 shows electrophoretic patterns of $D_1$ Peptide. The $D_1$ Peptide, isolated by Sepharose-fibrin monomer affinity chromatography of the Sephadex G-100 pool III (see FIG. 1), was labeled with 125-Iodine, then electrophoresed on polyacrylamide (12.5%) gels under reducing conditions. The gel was sliced (2 mm/slice) and the radioactivity measured. A duplicate gel was stained with Coomassie Brilliant Blue.

Affinity chromatography of peptides from Peaks II or III on the Sepharose-insolubilized fibrin-monomer column bound approximately 8% or 40%, respectively, of the protein. On 12.5% polyacrylamide gel electrophoresis of the bound material from either peak, a single band of approximately 5,000 molecular weight was seen (FIG. 2).

This $D_1$ Peptide was labeled with 125-Iodine by the chloramine-T method. Approximately 500 μg of peptide in 0.2 ml 0.15M Tris-HCl pH 7.8 was incubated with 1 mCi carrier-free Na$^{125}$I and 1 mg chloramine T for 30 sec. at room temperature. The reaction was stopped by the addition of 1 mg sodium metabisulfite followed by gel filtration of the preparation on a BioGel P-2 column (0.6×30 cm) in 10% acetic acid. An aliquot of the labeled peptide was electrophoresed on 12.5% polyacrylamide gels which were sliced and counted (FIG. 2). A single band of radioactivity which corresponded in mobility to the 5000 molecular weight peptide was present. This $D_1$ Peptide isolated by affinity chromatography on insolubilized fibrin monomer was later shown to originate from the $\gamma$ chain of the Fragment D region of fibrinogen.

Inhibition of fibrin monomer polymerization

Fibrin monomer was prepared according to the method of Belitser et al, *Biochem. Biophys. Acta* 154, 367–375 (1968) using either thrombin or batroxobin (an enzyme from the venom of *Bothrops atrox*). The polymerization of fibrin monomer which was formed by batroxobin (lacking fibrinopeptide A) or by thrombin (lacking fibrinopeptides A and B) was inhibited by $D_1$ Peptide. Polymerization was measured spectrophotometrically at 350 nm as has been described in Budzynski, *Biochem. Biophys. Acta* 584, 284–287 (1979). To measure the effect of $D_1$ Peptide on the rate of thrombin fibrin monomer polymerization, a 0.19 ml aliquot of either 0.05M Tris-HCl, 0.1M NaCl pH 7.55 or 0.19 ml of the buffer containing $D_1$ Peptide was put into a quartz cell and the baseline recorded. At zero time the recorder was started and 0.01 ml of fibrin monomer (1.5 mg/ml in 0.02M acetic acid) was added, the cells were inverted, and the increase in absorbance at 350 nm was measured continuously for 15 min or until plateau levels were reached. For batroxobin fibrin monomer 0.15 ml of buffer or buffer containing $D_1$ Peptide was mixed with 0.05 ml of batroxobin fibrin monomer (1.5 mg/ml in 0.02M acetic acid). The initial rate of polymerization was calculated from the slope of the steepest part of the curve and expressed as the increase in absorbance per min ($A_{350}\cdot\text{min}^{-1}$).

Figure 3:
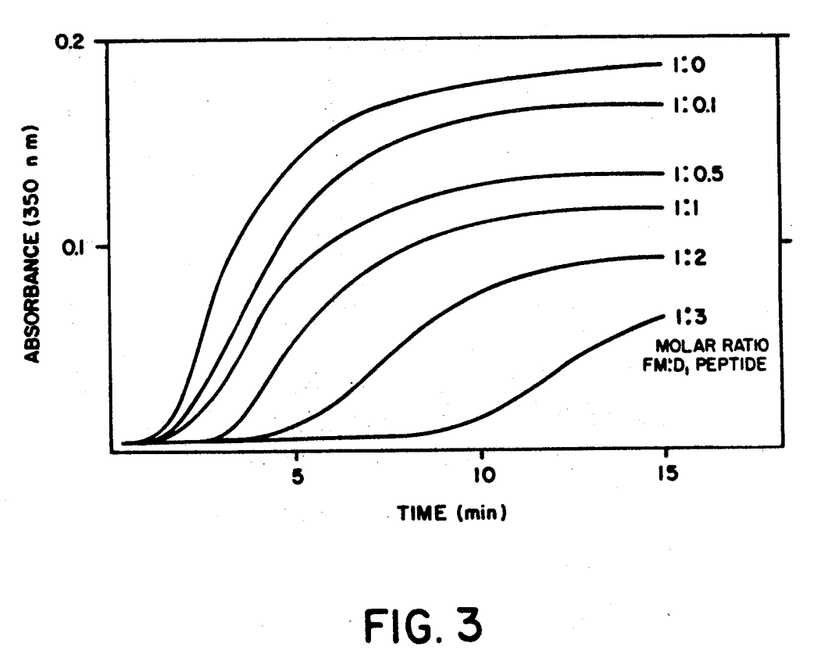
Figure 4:
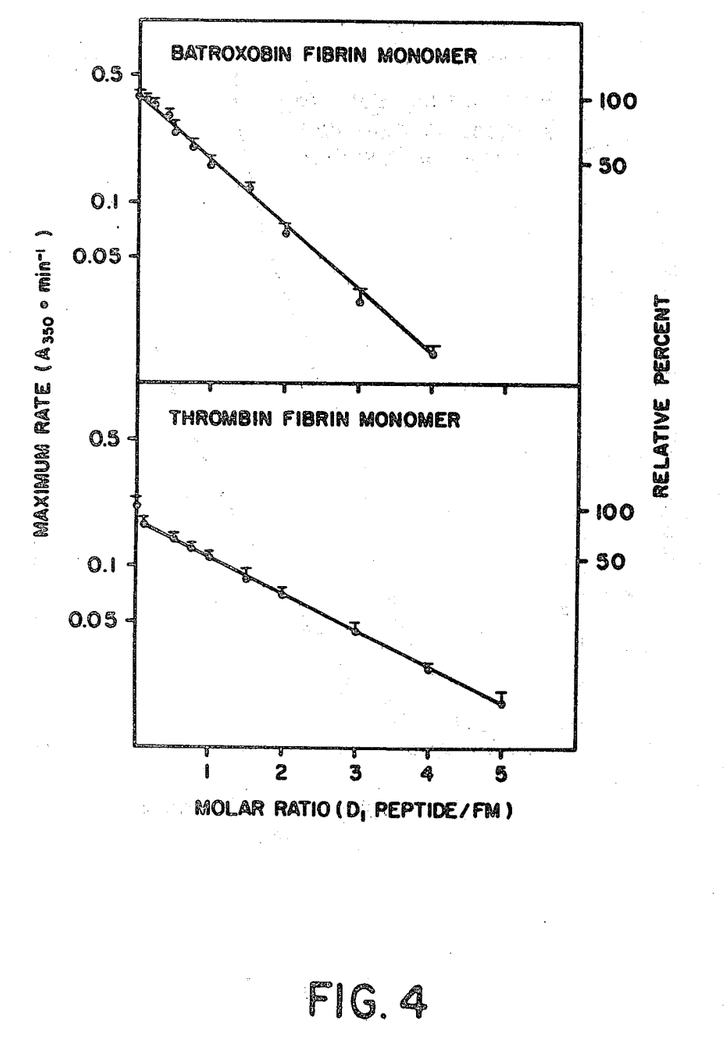
FIG. 4 shows dependence of polymerization inhibition on $D_1$ Peptide concentration. The effect of the $D_1$ Peptide on batroxobin (upper) and thrombin (lower) fibrin monomer was tested at various molar ratios. Each determination was done in triplicate and the mean and standard deviation of the logarithm of the maximum rate was plotted against the molar ratio.

As the molar ratio of $D_1$ Peptide to fibrin monomer increased, the maximum rate and extent of polymerization at 15 min. decreased proportionally while the lag time increased (FIG. 3). The effect of $D_1$ Peptide on the maximum rate of thrombin or batroxobin fibrin monomer polymerization at various molar ratios indicated that the maximum rate of polymerization was decreased by 50% at approximately a 1:1 molar ratio (FIG. 4). The data indicate that $D_1$ Peptide interacts with fibrin monomer at a binding site that becomes available on the fibrin monomer after the cleavage of fibrinopeptide A, and that two molecules of $D_1$ Peptide combine with one molecule of fibrin monomer.

Figure 5:
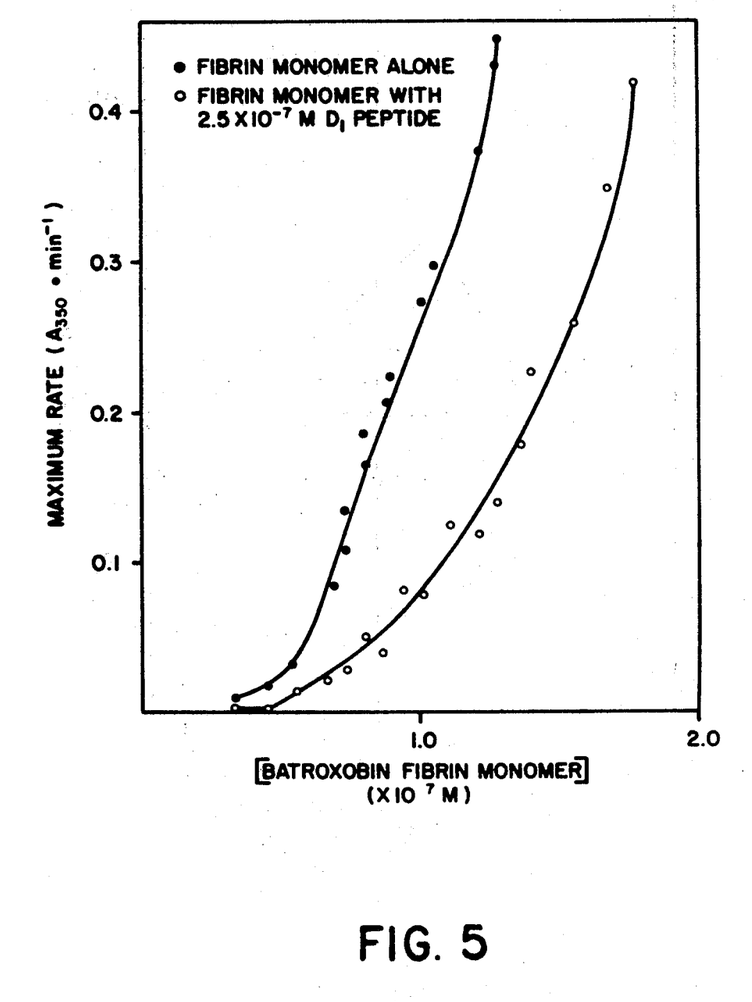
FIG. 5 shows the effect of the $D_1$ Peptide on the maximum polymerization rate of batroxobin fibrin monomer. The concentration of fibrin monomer was varied from $3.3 \times 10^{-8}$M to $1.75 \times 10^{-7}$M and the maximum rate of polymerization determined in the absence (.) or presence (0) of $2.5 \times 10^{-7}$M $D_1$ Peptide.

In order to assess the effect of $D_1$ Peptide on fibrin monomer polymerization over a wide range of concentrations, batroxobin fibrin monomer concentration was varied from $3.3\times10^{-8}$M to $1.75\times10^{-7}$M and the maximum rate of polymerization measured in the absence or presence of $2.5\times10^{-7}$M $D_1$ Peptide (FIG. 5). The polymerization of fibrin monomer appears to resemble a condensation reaction since as its concentration increases the $V_{max}$ and $K_m$ values approach infinity. Therefore the measure of inhibitory potential or $K_I$ of $D_1$ Peptide cannot be derived from the kinetic data. The effect of $D_1$ Peptide is to decrease the apparent concentration of polymerizable species of fibrin monomer. For example, to achieve a maximum rate of $0.2\ A_{350} \cdot min^{-1}$, the concentration of batroxobin fibrin monomer is $7.8 \times 10^{-8}M$. However, at a $D_1$ Peptide concentration of $2.6 \times 10^{-7}M$, the concentration of fibrin monomer necessary to achieve the same ratio of polymerization (apparent; [FM]) is $1.42 \times 10^{-7}M$. Therefore the $D_1$ Peptide appears to decrease the concentration of fibrin monomer and acts as a competitive inhibitor of polymerization.

Equilibrium binding of $D_1$ Peptide

To measure the number of binding sites and the strength of the interaction, the binding of $D_1$ Peptide to $NH_2$-terminal disulfide knot (NDSK), thrombin-treated NDSK, fibrinogen, fibrin monomer, and Fragment $D_1$ was tested. NDSK is a cyanogen bromide fragment of fibrinogen which contains the intact $NH_2$-terminal region of all six polypeptide chains. Since this fragment does not self-polymerize, it was used as a tool to measure the binding of $D_1$ Peptide to the $NH_2$-terminal region of fibrinogen after thrombin treatment.

$NH_2$-terminal disulfide knot (NDSK) was prepared from a cyanogen bromide digest of fibrinogen as has been described in Olexa et al, *J. Biol. Chem.* 254, 4925–4932 (1979) and Blomback et al, *Nature* 218, 130–134 (1968), which are hereby incorporated by reference. NDSK (10 mg) was dialyzed against 0.15M Tris-HCl, 10 mM calcium chloride pH 7.8 then incubated with 10 units of thrombin for 4 hrs. at 37° C. Under these conditions both fibrinopeptides A and B are removed as determined by the analysis of the $NH_2$-terminal amino acids.

Binding studies were done using either the classical equilibrium dialysis technique with dialysis tubing in small test tubes or the Sephadex gel equilibrium technique described in Hirose et al, *Biochem. Biophys. Acta* 133, 376–379 (1979). Equilibrium dialysis was done in small test tubes using standard dialysis tubing. NDSK, thrombin-treated NDSK, fribrinogen or Fragment $D_1$ in final concentrations ranging from $4.4 \times 10^{-7}M$ to $2 \times 10^{-5}M$ in 0.5 ml of 0.15M Tris-HCl, pH 7.8 was dialyzed against 1.0 ml of buffer containing 125-I labeled $D_1$ peptide ($4.4 \times 10^{-7}M$–$2 \times 10^{-5}M$ final concentration) at room temperature for 18 hrs. The volume of solutions inside and outside the tubing was quantitated and aliquots were counted. Results were verified using the Sephadex gel equilibration procedure of Hirose et al using Sephadex G-25 prewashed with 50% acetic acid, distilled water, and ethanol, then dried. In conical centrifuge tubes 0.1 mg of dry Sephadex G-25 was reswollen in 0.75 ml of 0.15M Tris-HCl pH 7.4 containing 1.0 mg/ml bovine serum albumin. Conditions were established such that the polymerization of fibrin monomer was inhibited by $D_1$ Peptide. In a final volume of 1.0 ml, thrombin or batroxobin fibrin monomer ($1 \times 10^{-8}M$ fina concentration) was mixed with 125-I labeled $D_1$ Peptide ($2 \times 10^{-6}M$ to $2 \times 10^{-5}M$ final concentration) which was pre-equilibrated in Sephadex G-25 swollen in 0.05M Tris-HCl, 0.1M NaCl pH 7.55. The molar ratio of $D_1$ Peptide to fibrin monomer in each experiment was greater than 100 to 1.

To summarize this technique, 125-I $D_1$ peptide was incubated with Sephadex G-25 for 15 min., at which time equilibrium was achieved. The species to be tested was added and equilibrium again established. An aliquot of the supernatant was removed and counted. The outside volume was determined using 125-I fibrinogen. The amounts of bound and free peptide were calculated according to the method described in Hirose et al. In the Sephadex gel method, equilibrium is established very quickly, usually within 10 min., a feature that allowed some experiments to be done testing the interactions of $D_1$ Peptide with fibrin monomer. For NDSK, thrombin-treated NDSK, fibrinogen and Fragment $D_1$, results from the two methods, equilibrium dialysis and Sephadex gel equilibrium, were comparable. Binding data from equilibrium dialysis and gel equilibration procedure were analyzed according to the Scatchard equation. Binding experiments with Fragment $D_1$, NDSK (untreated, thrombin-treated and batroxobin-treated) and with fibrinogen were done similarly.

Figure 6:
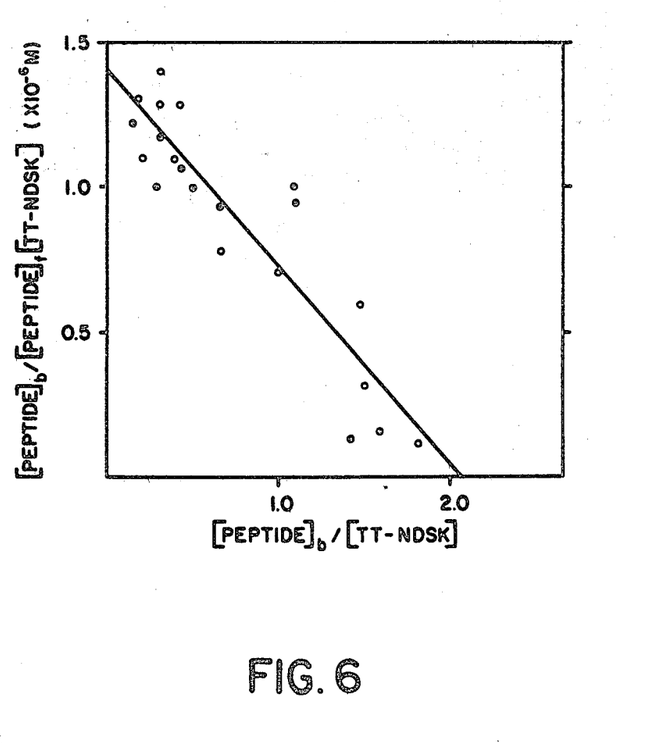
FIG. 6 shows a Scatchard analysis of binding data using the 125-I labeled $D_1$ Peptide ([Peptide]) and thrombin treated NH$_2$-terminal disulfide knot ([TT-NDSK]). Binding was tested using either the equilibrium dialysis method (.) or the Sephadex gel equilibrium method (0). The ratio of the number of the $D_1$ Peptide molecules bound per molecule of thrombin-treated NDSK is plotted on the abscissa. On the ordinate, the ratio of bound to free $D_1$ Peptide is given. The line was computed from a least square regression analysis of the data points.

There was no measurable binding of $D_1$ Peptide to intact NDSK, to fibrinogen, to Fragment $D_1$ or to bovine serum albumin. However, $D_1$ Peptide bound to NDSK which was pretreated with thrombin to remove fibrinopeptides A and B. The data (FIG. 6) indicate that there are approximately 2.1 binding sites on thrombin-treated NDSK with a $K_d$ of $1.45 \times 10^{-6}M$. Since the Scatchard method of data analysis has the dependent variable on both the x and y axes, the data was reported as 1/free ligand vs. total NDSK/bound protein. The parameters obtained from this plot were 2.2 for n, and $1.6 \times 10^{-6}M$ for Kd.

The purification of NDSK involves incubation of fibrinogen in cyanogen bromide in the presence of 70% formic acid. This treatment may alter the binding sites. Therefore, an attempt was made to reproduce the data using fibrin monomer instead of thrombin-treated NDSK. A major difficulty, the self-polymerization of fibrin monomer, was overcome by using high molar ratios of $D_1$ Peptide to fibrin monomer. However, in this situation the concentration of $D_1$ Peptide could be varied only over a small range of concentrations. $D_1$ Peptide was added to the Sephadex gel equilibrium system and incubated for 10 min., then soluble fibrin monomer was added in a molar excess of $D_1$ Peptide to fibrin monomer of 100–1000 fold. Under these conditions the lag time in the fibrin monomer polymerization was more than 30 min.

After 10 min. of incubation an aliquot of the supernatant was removed and counted. From these data the number of binding sites on the fibrin monomer molecule could be calculated. However, since the concentration of $D_1$ Peptide could be varied only within one order of magnitude as $D_1$ Peptide was acting as a competitive inhibitor of the native site on the D region of fibrin monomer, the dissociation constant could not be derived. In experiments using thrombin fibrin monomer the number of binding sites for $D_1$ Peptide was $1.82 \pm 0.26$ (15 experiments, mean and standard deviation). For batroxobin fibrin monomer the number of binding sites was $1.91 \pm 0.24$ (17 experiments, mean and standard deviation). The data are in agreement with the thrombin-treated NDSK experiments, indicating that the $NH_2$-terminal region of fibrin monomer contains two binding sites for $D_1$ Peptide and that both sites are revealed by the loss of fibrinopeptide A.

Total amino acid composition

Approximately 50 nmoles of $D_1$ Peptide in the presence of 50 nmoles of norleucine were hydrolyzed in 0.2 ml of concentrated hydrochloric-propionic acid under vacuum at 110° C. for 24, 48 and 72 hrs. The hydrolysate was analyzed in an automatic amino acid analyzer. The concentration of each amino acid was calculated by extrapolation of the concentrations at various hydrolysis times. The resulting values are presented in Table 1, where they are compared to the amino acid composition of the COOH-terminal segment of the γ chain 373–410.

The conversion of Fragment $D_1$ to $D_3$ results in cleavages of the COOH- and NH-terminal regions of the γ chain remnant. Thus, $D_1$ Peptide could have originated from either of these two regions. The $NH_2$-terminal of the γ chain has a large region devoid of glycine between residues 24 and 150. Also, there are no phenylalanine residues between position 28 and 168 in the γ chain. The presence of a valine in the peptide suggests that it may extend to the terminal residue, 410 valine, of the γ chain.

TABLE 1
TOTAL AMINO ACID COMPOSITION OF $D_1$ PEPTIDE

| Amino Acid | $D_1$ PEPTIDE Residues/100 | $D_1$ PEPTIDE Minimum Residues | γ 373–410[a] Residues/100 | γ 373–410[a] Minimum Residues |
|---|---|---|---|---|
| Asp[b] | 15.5 | 7 | 5.3 | 2 |
| Thr | 9.0 | 4 | 10.5 | 4 |
| Ser | 4.4 | 2 | 2.6 | 1 |
| Glu[b] | 9.0 | 4 | 10.5 | 4 |
| Pro | 2.2 | 1 | 2.6 | 1 |
| Gly | 13.3 | 6 | 13.2 | 5 |
| Ala | 6.7 | 3 | 5.3 | 2 |
| Cys | 0 | 0 | 0 | 0 |
| Val | 2.2 | 1 | 2.6 | 1 |
| Met | 4.4 | 2 | 5.3 | 2 |
| Iso | 6.7 | 3 | 7.9 | 3 |
| Leu | 4.4 | 2 | 5.3 | 2 |
| Tyr | 4.4 | 2 | 2.6 | 1 |
| Phe | 2.2 | 1 | 2.6 | 1 |
| His | 2.2 | 1 | 5.3 | 2 |
| Lys | 9.0 | 4 | 10.5 | 4 |
| Arg | 4.4 | 2 | 5.3 | 2 |
| Trp | — | — | 2.6 | 1 |
| TOTAL | | 45 | | 38 |
| Minimum Mol. wt. | 4674 | | 4281 | |

[a]Based on the amino acid sequence of the γ chain of fibrinogen.
[b]Aspartic acid and glutamic acid values include asparagine and glutamine, respectively.

$NH_2$-Terminal Amino Acid Sequence of the $D_1$ Peptide

The $NH_2$-terminal amino acid sequence was determined by the method of Edman et al as described in *Molecular Biol. Bochem. Biophys.* 8, 232–279 (1975) as modified by Tarr in *Anal. Biochem.* 63, 361–370 (1975). The PTH-amino acids were analyzed on 5×5 cm polyamide sheets according to the method of Kulbe as described in *Anal. Biochem.* 44, 548–558 (1971) and *Anal. Biochem.* 59, 564–573 (1974) with the modification of Summers et al described in *Anal. Biochem.* 53, 624–628 (1973). Only the three terminal amino acids were determined. The amino acids determined, threonine-arginine-tyrosine, correspond to the residues 373–375 of the fibrinogen γ chain. This sequence does not appear again throughout the γ chain.

COOH-Terminal Amino Acid Sequence of the $D_1$ Peptide

The COOH-terminal amino acid sequence was determined by sequential removal of amino acids from the carboxy-terminal end using carboxypeptidase Y. Approximately 25 n moles of $D_1$ Peptide were incubated with carboxypeptidase Y (100:1 w/w) in 0.1M sodium acetate buffer, pH 5.0 at room temperature for 30 mins., 1, 2, 3, 4 or 5 hours. The reaction was stopped by heating at 100° C. for 3 min. The material was freeze-dried, dissolved in 0.2M sodium citrate buffer, pH 2.2, filtered and applied to the amino acid analyzer.

For controls, carboxypeptidase Y was incubated similarly but without $D_1$ Peptide, to measure autolysis of the enzyme. The 0 time control was done by adding Peptide and enzyme to boiling buffer. The concentration of each amino acid was calculated, then background and 0 time levels were subtracted.

Figure 7:
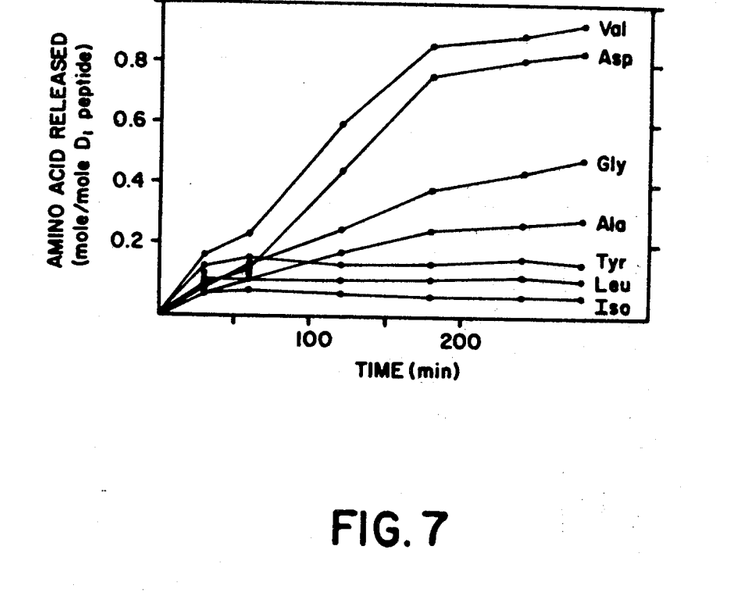
FIG. 7 shows the amino acids released from the carboxy-terminal region of the $D_1$ Peptide by carboxy-peptidase Y at various incubation times. The amino acids taken under consideration are those whose concentration increases with incubation time. The amino acids which do not show such feature may be derived from contaminations of the enzyme preparation.

The release of the amino acids at each time point are illustrated in FIG. 7. The data indicate that the COOH-terminal sequence of the Peptide is alanine-glycine-aspartic acid (or asparagine)-valine, corresponding to the residues 407–410 of the fibrinogen γ chain. The entire sequence of $D_1$ Peptide, based on the published sequence of the γ chain, has been given previously.

Having now fully described the invention, it will be evident to one of ordinary skill in the art that many changes and modifications can be made thereto without departing from the spirit or scope of the invention as set forth herein.

We claim:

1. A purified peptide having the amino acid sequence (a) Gln-Ala-Gly-Asp-Val, (b) Thr-Arg-Trp-Tyr-Ser-Met-Lys-Lys-Thr-Thr-Met-Lys-Ile-Ile-Pro-Phe-Asn-Arg-Leu-Thr-Ile-Gly-Glu-Gly-Gln-Gln-His-His-Leu-Gly-Gly-Ala-Lys-Gln-Ala-Gly-Asp-Val or (c) a purified peptide having an amino acid sequence intermediate between said amino acid sequences (a) and (b).

2. A purified peptide having the amino acid sequence X-Gln-Ala-Gly-Asp-Val, wherein X represents Ala-Lys-, Lys-, or the absence of an amino acid.

3. A purified peptide having substantially the amino acid sequence disclosed in claim 1(a), 1(c), or 2 wherein said purified peptide has a binding affinity for fibrin of at least 5% of that demonstrated by the amino acid sequence disclosed in claim 1(b).

4. A purified peptide having the amino acid sequence Thr-Arg-Trp-Tyr-Ser-Met-Lys-Lys-Thr-Thr-Met-Lys-Ile-Ile-Pro-Phe-Asn-Arg-Leu-Thr-Ile-Gly-Glu-Gly-Gln-Gln-His-His-Leu-Gly-Gly-Ala-Lys-Gln-Ala-Gly-Asp-Val.

5. A method of preparing a peptide inhibitor of fibrin monomer polymerization, comprising the steps of: degrading Fragment $D_1$ of fibrinogen with plasmin to form plasmin degradation products; separating said peptide inhibitor from plasmin degradation products of different molecular weights to give a partially purified peptide inhibitor; and isolating said peptide inhibitor from other peptides in said partially purified inhibitor by means of said peptide inhibitor's binding affinity for fibrin monomer.

6. The method of claim 5, wherein said separating comprises gel filtration.

7. The method of claim 6, wherein said gel filtration is carried out using dextran gel beads.

8. The method of claim 7, wherein said dextran gel beads have a dry diameter of 40–120μ and are eluted with an acetic acid solution.

9. The method of claim 5, wherein said separating comprises affinity chromatography.

10. The method of claim 9, wherein said affinity chromatography is carried out with fibrin monomer insolubilized on cyanogen bromide-activated agarose.

11. The method of claim 10, wherein said isolating comprises:
applying said partially purified peptide inhibitor to said agarose in a buffer having a pH between 6 and 8;
washing said agarose with said buffer; and
eluting said peptide inhibitor with an acid, base or high-salt solution.

12. A peptide inhibitor of fibrin monomer polymerization prepared by the process of claims 5, 8 or 11.

13. A method of inhibiting blood clotting comprising the steps of administering to a human or animal an amount of the peptide inhibitor of fibrin monomer polymerization prepared by the process of claims 5, 8 or 11, sufficient to increase blood clotting time.

14. A method of inhibiting blood clotting comprising adding to a container of blood an amount of the peptide inhibitor of fibrin monomer polymerization prepared by the process of claims 5, 8 or 11.

15. A method of inhibiting blood clotting comprising the step of administering to a human or animal an amount of the purified peptide of claim 1 sufficient to increase blood clotting time.

16. A method of detecting a thrombus comprising the step of administering to a human or animal an amount of the peptide inhibitor of fibrin monomer polymerization prepared by the process of claims 5, 8 or 11 labeled with a gamma-emitting radioisotope sufficient to allow external detection of the location of said thrombus.

17. A method of detecting a thrombus comprising the step of administering to a human or animal an amount of the purified peptide of claim 1 labeled with a gamma-emitting radioisotope sufficient to allow external detection of the location of said thrombus.

18. A purified peptide having the amino acid sequence described in claim 1, wherein said purified peptide is labeled with a gamma-emitting radioactive isotope or an X-ray contrast agent.

19. The peptide inhibitor of fibrin monomer polymerization prepared by the process of claims 5, 8 or 12 wherein said peptide inhibitor is labeled with a gamma-emitting radioactive isotope or an X-ray contrast agent.

20. A composition suitable for intravenous injection, comprising:
the purified peptide of claims 1 or 18; and
a pharmaceutically acceptable carrier.

21. A composition suitable for intravenous injection comprising: a peptide inhibitor of fibrin monomer polymerization prepared by the process of claims 5, 8 or 12; and a pharmaceutically acceptable carrier.

22. A radioactive composition suitable for intravenous injection, comprising: a peptide inhibitor of fibrin monomer polymerization prepared by the process of claim 5, 8 or 11 wherein a gamma-emitting radioactive isotope is covalently attached to said purified peptide; and a pharmaceutically acceptable carrier.

23. A method of detecting a thrombus comprising the step of administering to a human or animal an amount of the peptide inhibitor of fibrin monomer polymerization of claims 5, 8 or 11 labeled with an X-ray contrast agent sufficient to cast an X-ray shadow.

24. A method of detecting a thrombus comprising the step of administering to a human or animal an amount of the purified peptide of claim 1 labeled with an X-ray contrast agent sufficient to cast an X-ray shadow of said thrombus.

* * * * *